(12) United States Patent
Robinson et al.

(10) Patent No.: US 11,878,107 B2
(45) Date of Patent: Jan. 23, 2024

(54) SYSTEMS, APPARATUSES, AND METHODS FOR NEGATIVE-PRESSURE TREATMENT WITH REDUCED TISSUE IN-GROWTH AND EXTENDED WEAR TIME

(71) Applicant: KCI Licensing, Inc., San Antonio, TX (US)

(72) Inventors: Timothy Mark Robinson, Shillingstone (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 76 days.

(21) Appl. No.: 17/620,351

(22) PCT Filed: Jun. 9, 2020

(86) PCT No.: PCT/US2020/036777
§ 371 (c)(1),
(2) Date: Dec. 17, 2021

(87) PCT Pub. No.: WO2020/257000
PCT Pub. Date: Dec. 24, 2020

(65) Prior Publication Data
US 2022/0362062 A1    Nov. 17, 2022

Related U.S. Application Data

(60) Provisional application No. 62/864,164, filed on Jun. 20, 2019.

(51) Int. Cl.
*A61M 1/00*       (2006.01)
*A61F 13/02*     (2006.01)

(52) U.S. Cl.
CPC ......... *A61M 1/915* (2021.05); *A61F 13/0216* (2013.01); *A61M 1/916* (2021.05)

(58) Field of Classification Search
CPC .... A61M 1/915; A61M 1/916; A61F 13/0216
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Kai H Weng
*Assistant Examiner* — Nhu Q. Tran

(57) ABSTRACT

Dressings, systems, and methods for treating a tissue site with negative pressure are described. The dressing includes a manifold having a first surface and a second surface opposite the first surface, a first layer adjacent to the first surface, and a second layer adjacent to the second surface. The first layer and the second layer each are formed from a polymer film. A plurality of fluid restrictions are formed in the polymer film adjacent to at least the first surface. A first plurality of bonds is formed between the first layer and the second layer. The first plurality of bonds define separable sections of the manifold. A second plurality of bonds is formed between the first layer and the second layer. The second plurality of bonds define a plurality of openings.

16 Claims, 10 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2014/0163491 A1 | 6/2014 | Schuessler et al. |
| 2015/0080788 A1 | 3/2015 | Blott et al. |
| 2015/0119834 A1* | 4/2015 | Locke ............... A61F 13/0216 156/247 |
| 2018/0110657 A1* | 4/2018 | Locke ................ A61F 13/023 |
| 2019/0231600 A1* | 8/2019 | Locke ................ A61M 1/915 |
| 2020/0139025 A1* | 5/2020 | Robinson ........... A61M 1/915 |
| 2020/0170842 A1* | 6/2020 | Locke ............ A61F 13/00068 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |

(56) References Cited

FOREIGN PATENT DOCUMENTS

| WO | 96/05873 A1 | 2/1996 |
|---|---|---|
| WO | 97/18007 A1 | 5/1997 |
| WO | 99/13793 A1 | 3/1999 |
| WO | 2017119996 A1 | 7/2017 |
| WO | 2018226650 A1 | 12/2018 |
| WO | 2019027731 A1 | 2/2019 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, p. 24.

Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion Corresponding to Application No. PCT/US2020/036777, dated Sep. 17, 2020.

\* cited by examiner

SYSTEMS, APPARATUSES, AND METHODS FOR NEGATIVE-PRESSURE TREATMENT WITH REDUCED TISSUE IN-GROWTH AND EXTENDED WEAR TIME

RELATED APPLICATION

The present application claims priority to U.S. Provisional Patent Application No. 62/864,164, filed Jun. 20, 2019, which is incorporated herein by reference for all purposes.

TECHNICAL FIELD

The invention set forth in the appended claims relates generally to tissue treatment systems and more particularly, but without limitation, to systems, dressings, and fillers for negative-pressure tissue treatment, and methods of using systems, dressings, and fillers for negative-pressure tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, a dressing for treating a tissue site with negative pressure can be described. The dressing can include a manifold having a first surface and a second surface opposite the first surface. The dressing can also include a first layer adjacent to the first surface and a second layer adjacent to the second surface. The first layer and the second layer each can comprise a polymer film. A plurality of fluid restrictions can be disposed in the polymer film adjacent to at least the first surface. A first plurality of bonds can be formed between the first layer and the second layer. The first plurality of bonds may define separable sections of the manifold. A second plurality of bonds can be formed between the first layer and the second layer. The second plurality of bonds can define a plurality of openings.

More generally, in some embodiments, a tissue interface for treating a tissue site with negative pressure can be described. The tissue interface can include a foam having a first surface and a second surface opposite the first surface. A first polymer film can be positioned adjacent to the first surface, and a second polymer film can be positioned adjacent to the second surface. A plurality of slits can be formed in the polymer film adjacent to at least the first surface. And a means for bonding the first polymer film to the second polymer film to form separable sections of the foam and a plurality of holes can be provided.

Other example embodiments may relate to an apparatus for providing negative-pressure treatment to a tissue site. The apparatus can include a manifold having a first side and a second side opposite the first side. A first layer can be positioned adjacent to the first side, and a second layer can be positioned adjacent to the second side. The first layer and the second layer can each comprise a polymer film. A plurality of fluid restrictions can be formed in the polymer film adjacent to at least the first side. A plurality of bonds can be formed between the first layer and the second layer, the plurality of bonds defining separable sections of the manifold and a plurality of openings. And a negative-pressure source can be fluidly coupled to the manifold.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

Figure 1:
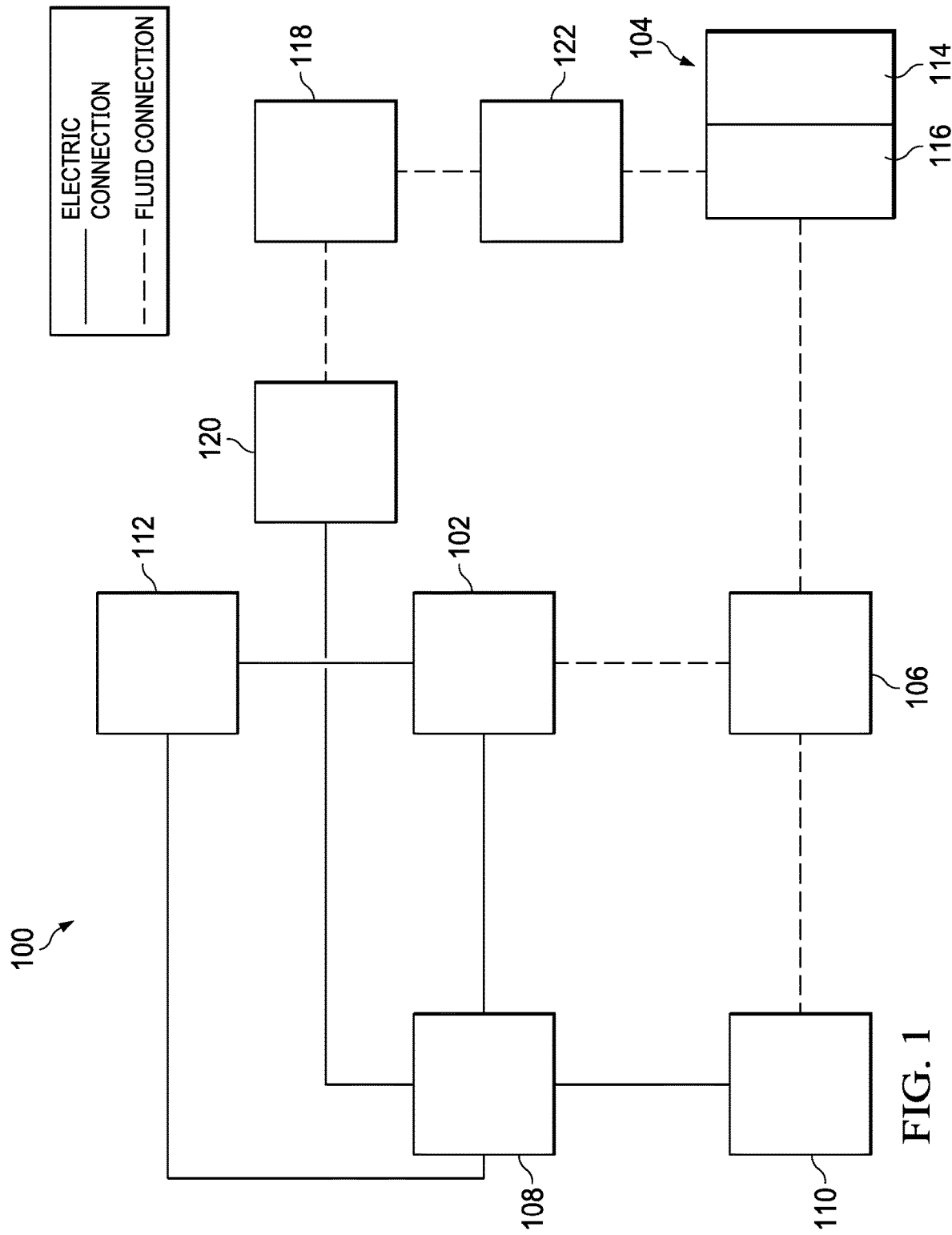
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy with instillation of topical treatment solutions to a tissue site in accordance with this specification. The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a pressure sensor 110, an electric sensor 112, or both, coupled to the controller 108. As illustrated in the example of FIG. 1, the dressing 104 may comprise or consist essentially of a tissue interface 114, a cover 116, or both in some embodiments.

The therapy system 100 may also include a source of instillation solution. For example, a solution source 118 may be fluidly coupled to the dressing 104, as illustrated in the example embodiment of FIG. 1. The solution source 118 may be fluidly coupled to a positive-pressure source such as the positive-pressure source 120, a negative-pressure source such as the negative-pressure source 102, or both in some embodiments. A regulator, such as an instillation regulator 122, may also be fluidly coupled to the solution source 118 and the dressing 104 to ensure proper dosage of instillation solution (e.g. saline) to a tissue site. For example, the instillation regulator 122 may comprise a piston that can be pneumatically actuated by the negative-pressure source 102 to draw instillation solution from the solution source during a negative-pressure interval and to instill the solution to a dressing during a venting interval. Additionally or alternatively, the controller 108 may be coupled to the negative-pressure source 102, the positive-pressure source 120, or both, to control dosage of instillation solution to a tissue site. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108, and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108, and may be fluidly coupled to one or more distribution components to provide a fluid path to a tissue site. In some embodiments, components may also be coupled by virtue of physical proximity, being integral to a single structure, or being formed from the same piece of material. For example, the tissue interface 114 and the cover 116 may be discrete layers disposed adjacent to each other, and may be joined together in some embodiments.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the pressure sensor 110 or the electric sensor 112, are generally known in the art as any apparatus operable to detect or measure a physical phenomenon or property, and generally provide a signal indicative of the phenomenon or property that is detected or measured. For example, the pressure sensor 110 and the electric sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, the pressure sensor 110 may be a piezoresistive strain gauge. The electric sensor 112 may optionally measure operating parameters of the negative-pressure source 102, such as the voltage or current, in some embodiments. Preferably, the signals from the pressure sensor 110 and the electric sensor 112 are suitable as an input signal to the controller 108, but some signal conditioning may be appropriate. For example, the signal may need to be filtered or amplified before it can be processed by the controller 108. Typically, the signal is an electrical signal, but may be represented in other forms, such as an optical signal.

The tissue interface 114 can be generally adapted to partially or fully contact a tissue site. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least about 300 g/m$^2$ per twenty-four hours in some embodiments. In some example embodiments, the cover 116 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

The cover 116 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Coveris Advanced Coatings of Wrexham, United Kingdom having, for example, an MVTR (inverted cup technique) of about 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Glendale, California; polyether block polyamide copolymer (PEBAX), for example, from Arkema, France; INSPIRE 2327; or other appropriate material.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight between about 25 grams per square meter (g.s.m.) to about 65 g.s.m. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Some tissue sites can develop thick exudate. Thick exudate can inhibit negative-pressure therapy by filling and clogging flow passages in a dressing. Some dressing provide a reticulated felted foam having 1 cm diameter holes to permit the thick exudate to be freely removed from the tissue site. The felted foam can also reduce the rate of ingrowth into the dressing due to the reduced size of the pores of the felted foam. Often other similarly felted foam layers can be applied over a contact layer having the holes to complete the wound dressing treatment sequence. While felted foam can reduce ingrowth due to the reduction in pore size; felted foam can have an increased density, thereby increasing its stiffness. The increased stiffness may reduce the flexibility and ability of the felted foam to cover complex structures. The increased stiffness means that the felted foam structures must be sized to fill the wound, otherwise the felted foam may come into contact with intact skin, leading to maceration. Use of a felted foam may also increase the cost of the dressing due to its increased material density. A wound filler that allows free removal of thick exudate, is sizeable, and has a potential for an extended wear time due to fewer ingrowth characteristics, is flexible, and that may be placed over the periwound without risking maceration may lead to additional benefits to the healing process for patients.

Figure 2:
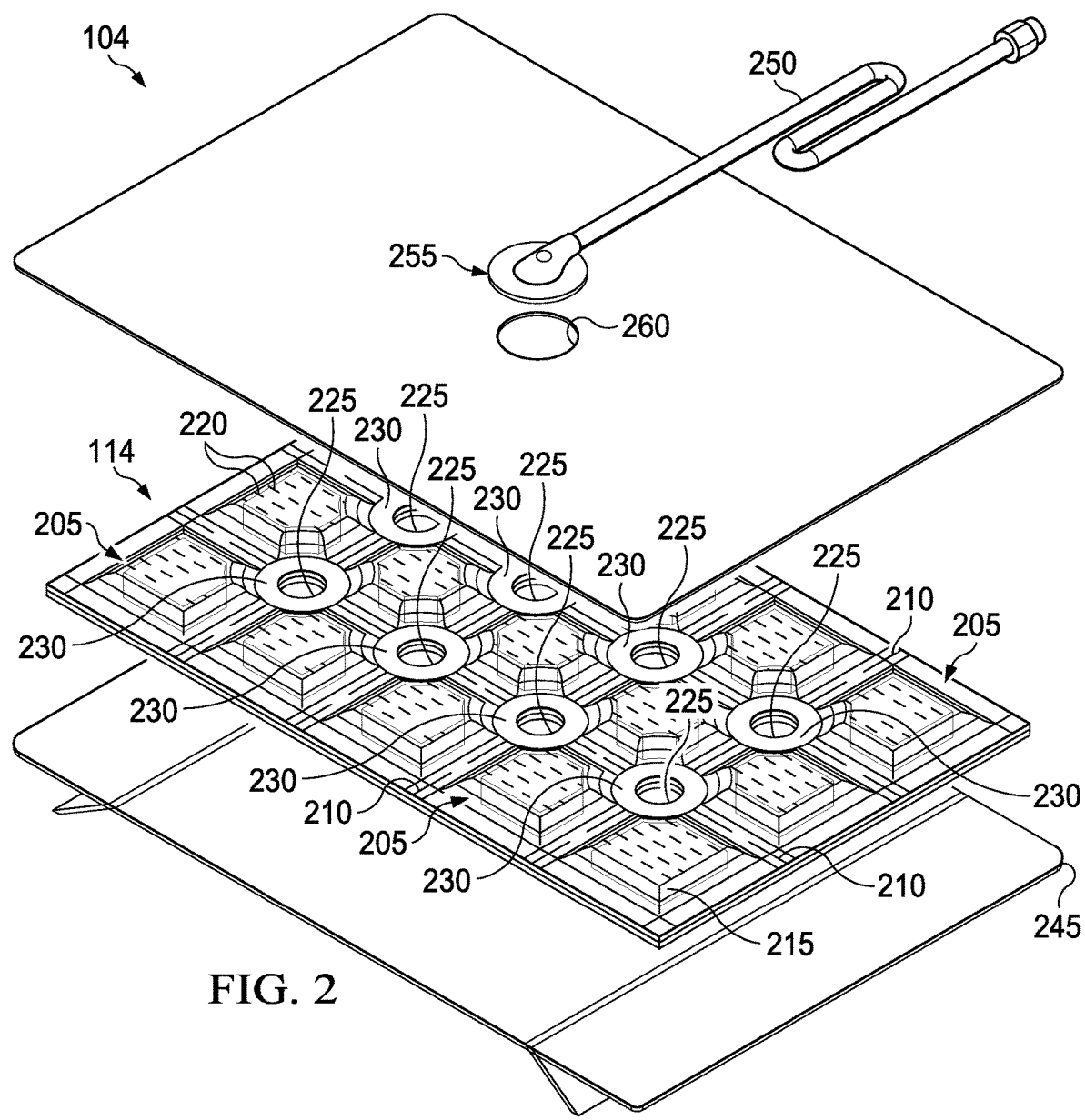
FIG. 2 is an exploded view of a dressing that may be associated with an example embodiment of the therapy system of FIG. 1.

FIG. 2 is an assembly view of an example of the dressing 104 of FIG. 1, illustrating additional details that may be associated with some embodiments in which the tissue interface 114 comprises separable sections. In the example of FIG. 2, the tissue interface 114 comprises one or more interface sections 205, which may be bounded by seams 210. Each of the interface sections 205 may include a manifold section 215. In some examples, seams 210 may be formed between or may define the manifold sections 215. In some embodiments, one or more openings 225 surrounded by welds 230 can be formed through the tissue interface 114.

The manifold sections 215 may comprise or consist essentially of foam in some embodiments. For example, the foam may be open-cell foam, such as reticulated foam. The foam may also be relatively thin and hydrophobic to reduce the fluid hold capacity of the dressing, which can encourage exudate and other fluid to pass quickly to external storage. The foam layer may also be thin to reduce the dressing profile and increase flexibility, which can enable it to conform to wound beds and other tissue sites under negative pressure. In some embodiments, the manifold sections 215 may be formed of 3-dimensional textiles, non-woven wicking material, vacuum-formed texture surfaces, and composites thereof. A hydrophobic manifold having a thickness of less than 7 millimeters and a free volume of at least 90% may be suitable for many therapeutic applications. In some embodiments, the manifold sections 215 may be formed of colored material. Each of the manifold sections 215 may be a same color or a different color.

As illustrated in the example of FIG. 2, the tissue interface 114 may have one or more fluid restrictions 220, which can be distributed uniformly or randomly across the tissue interface 114. The fluid restrictions 220 may be bi-directional and pressure-responsive. For example, each of the fluid restrictions 220 generally may comprise or consist essentially of an elastic passage that is normally unstrained to substantially reduce liquid flow, and can expand or open in response to a pressure gradient. The fluid restrictions 220 may be coextensive with the manifold sections 215.

For example, some embodiments of the fluid restrictions 220 may comprise or consist essentially of one or more slits, slots or combinations of slits and slots. In some examples, the fluid restrictions 220 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeters may also be acceptable. Such dimensions and tolerances may be achieved with a laser cutter, for example. In some embodiments, the fluid restrictions 220 may be formed by ultrasonics or other heat means. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

As illustrated in the example of FIG. 2, in some embodiments, the dressing 104 may include a release liner 245 to protect an optional adhesive on a portion of the cover 116 prior to use. The release liner 245 may also provide stiffness to assist with, for example, deployment of the dressing 104. The release liner 245 may be, for example, a casting paper, a film, or polyethylene. Further, in some embodiments, the release liner 245 may be a polyester material such as polyethylene terephthalate (PET), or similar polar semi-crystalline polymer. The use of a polar semi-crystalline polymer for the release liner 245 may substantially preclude wrinkling or other deformation of the dressing 104. For example, the polar semi-crystalline polymer may be highly orientated and resistant to softening, swelling, or other deformation that may occur when brought into contact with components of the dressing 104, or when subjected to temperature or environmental variations, or sterilization.

Further, a release agent may be disposed on a side of the release liner 245 that is configured to contact the tissue interface 114. For example, the release agent may be a silicone coating and may have a release factor suitable to facilitate removal of the release liner 245 by hand and without damaging or deforming the dressing 104. In some embodiments, the release agent may be a fluorocarbon or a fluorosilicone, for example. In other embodiments, the release liner 245 may be uncoated or otherwise used without a release agent.

FIG. 2 also illustrates one example of a fluid conductor 250 and a dressing interface 255. As shown in the example of FIG. 2, the fluid conductor 250 may be a flexible tube, which can be fluidly coupled on one end to the dressing interface 255. The dressing interface 255 may be an elbow connector, as shown in the example of FIG. 2, which can be placed over an aperture 260 in the cover 116 to provide a fluid path between the fluid conductor 250 and the tissue interface 114.

Figure 3:
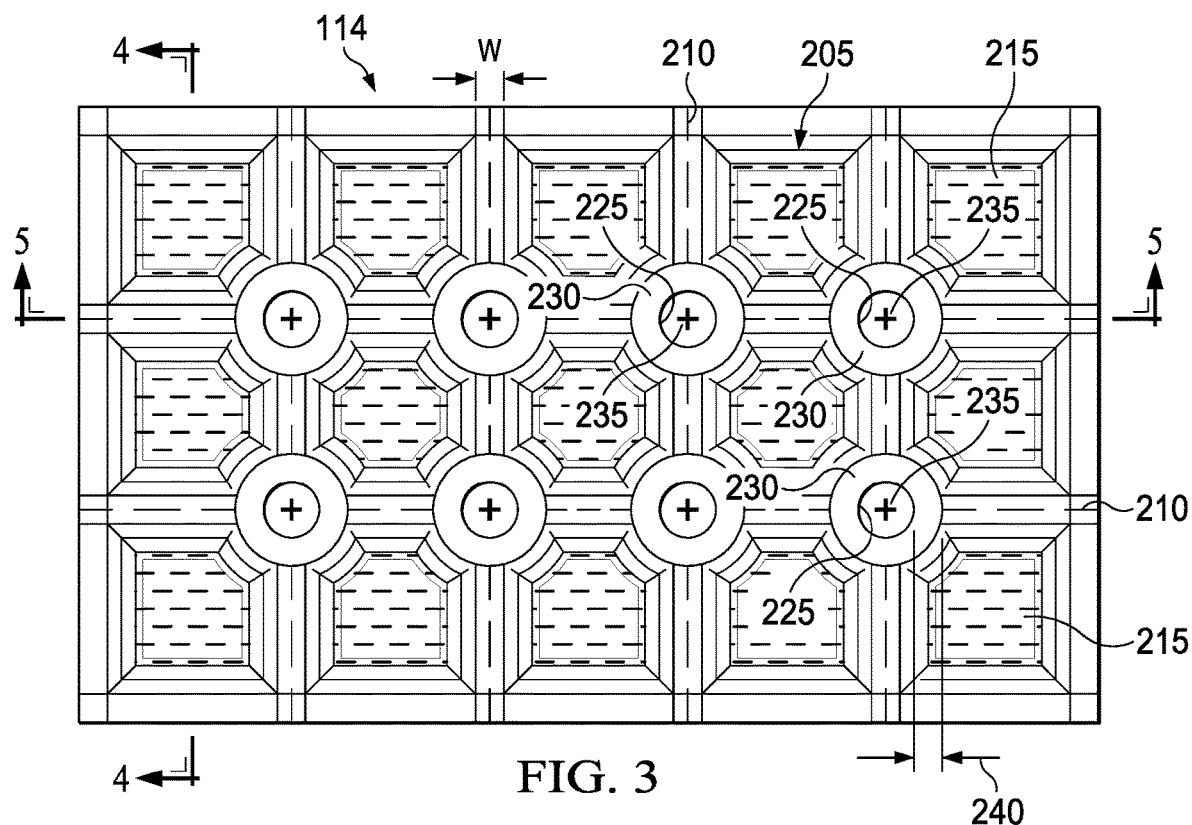
FIG. 3 is a top view of a tissue interface of the dressing of FIG. 2.

FIG. 3 is a top view of the tissue interface 114 of FIG. 2, illustrating additional details that may be associated with some example embodiments. The manifold sections 215 in each of the interface sections 205 may have a same shape or a different shape. As shown in the example of FIG. 3, the interface sections 205 and the manifold sections 215 may have similar shapes. In some embodiments, each of the interface sections 205 and the manifold sections 215 may have a tessellate shape, such as the generally square shape in the example of FIG. 3, with sides having a length ranging from about 10 mm to about 30 mm (e.g., about 15 mm to about 25 mm or about 18 mm to about 22 mm). For example, the manifold sections 215 may be squares having dimensions of about 20 mm by about 20 mm.

Each of the seams 210 may have a width W ranging from about 2 mm to about 5 mm, and may be wide enough to allow for the interface sections 205 to be separated along the seams 210 without exposing any portion of the manifold sections 215. In some embodiments, the seams 210 may be perforated. The perforations can be spaced to permit the interface sections 205 to be separated from each other along the perforation lines.

In some embodiments, the openings 225 can comprise or consist essentially of holes, apertures, flow channels, or perforations. In some embodiments, each opening 225 may have an average effective diameter between about 5 mm and about 10 mm. An effective diameter of a non-circular area may be a diameter of a circular area having the same surface area as the non-circular area. In some embodiments, the openings 225 may have a uniform size. In other embodiments, the openings 225 may have different sizes. The openings 225 can be circular, polygonal, elliptical, and amorphous shaped. In some embodiments, the openings 225 may have a uniform shape. In some embodiments, the openings 225 may be formed with sharp corners to create stress points in underlying tissue during use. In other embodiments, the openings 225 may have different shapes. For example, a portion of the openings 225 may have a first shape and a portion of the openings 225 may have a second shape that is different than the first shape. The openings 225 having different shapes may be distributed to vary the pattern of deformation in the underlying tissue with repeated placements of the tissue interface 114. In still other embodiments, each opening 225 may comprise an array of openings having a smaller diameter than the opening 225.

The openings 225 can be positioned at centers 235. A center 235 can be a position at which the opening 225 is symmetrical in at least one plane perpendicular to the surface of the center 235. In other embodiments, the center 235 can be a position at which the opening 225 is bisected by at least one plane perpendicular to the surface of the center 235 to have an equal area of the opening 225 on either side of the plane. In some embodiments, the centers 235 of the openings 225 can be at intersections of the seams 210. For example, seams 210 parallel to the width of the tissue interface 114 may be perpendicular to seams 210 running parallel to the length of the tissue interface 114. The seams 210 that are orthogonal to each other will intersect at right angles on the tissue interface 114, forming a grid having the manifold sections 215 disposed in cells of the grid formed by the seams 210. The centers 235 of the openings 225 can be at the intersections of the seams 210 and permit fluid flow across the tissue interface 114. In some embodiments, the openings 225 can permit the flow of thick exudate across the tissue interface 114. The openings 225 can have a pitch parallel to a length and width of the tissue interface 114. For example, the openings 225 can have a pitch parallel to the length of the tissue interface 114 between about 20 mm and about 40 mm and a pitch parallel to a width of the tissue interface 114 between about 20 mm and about 40 mm. The pitch parallel to the length and width of the tissue interface 114 may be at least about twice the average effective diameter of the openings 225 in the tissue interface 114.

In some embodiments, the openings 225 can be bounded by the welds 230. In some embodiments, the welds 230 can have a width 240 between about 2 mm to about 5 mm. For example, the width 240 of the weld 230 can be measured from a location on the weld 230 adjacent to the opening 225 to a closest location on the weld 230 peripheral to the opening 225. In some embodiments, the width 240 can be the difference between a radius of the opening 225 and a radius of the weld 230. In some embodiments, portions of the manifold sections 215 proximate to the welds 230 may be removed to accommodate the welds 230. For example, a manifold section 215 having a square shape may have a corner proximate to the welds 230. The corner of the manifold section 215 may be chamfered to accommodate the weld 230. In other embodiments, the corner of the manifold section 215 may be rounded or otherwise shaped to receive a portion of the weld 230. The welds 230 may be flexible and conformable without exposing unfused foam.

Figure 4:
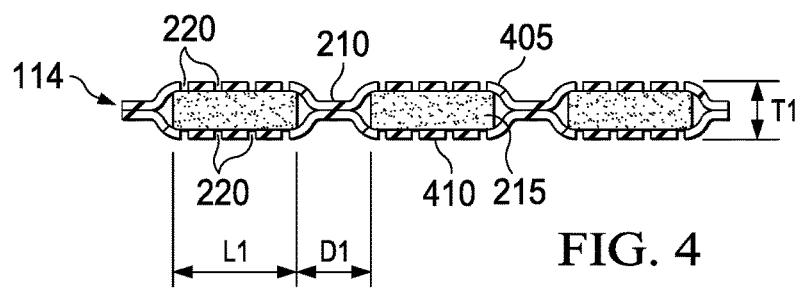
FIG. 4 is a cross-sectional view of the tissue interface of FIG. 3 taken along line 4-4.

FIG. 4 is a section view of the tissue interface 114 of FIG. 3 taken along line 4-4, illustrating additional details that may be associated with some embodiments. In the example of FIG. 4, the tissue interface 114 comprises a first layer 405, a second layer 410, and the manifold sections 215 disposed between the first layer 405 and the second layer 410. In some embodiments, the first layer 405 and the second layer 410 may be disposed adjacent to the manifold sections 215 as shown in the example of FIG. 4. Also as shown in the example of FIG. 4, the seams 210 may be formed by one or more bonds between the first layer 405 and the second layer 410. The bonds may be continuous or discrete.

The first layer 405 and the second layer 410 may comprise or consist essentially of a means for controlling or managing fluid flow. In some embodiments, the first layer 405 and the second layer 410 may comprise or consist essentially of an elastomeric material that is impermeable to liquid. For example, the first layer 405 and the second layer 410 may comprise or consist essentially of a polymer film. The first layer 405 and the second layer 410 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the second layer 410 may have a substantially flat surface, with height variations limited to 0.2 millimeters over a centimeter.

In some embodiments, the first layer 405 and the second layer 410 may comprise or consist essentially of a hydrophobic material. The hydrophobicity may vary, but may have a contact angle with water of at least ninety degrees. In some embodiments the hydrophobic material may have a contact angle with water of no more than 150 degrees. For example, the contact angle may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, VA, and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles reported herein represent averages of 5-9 measured values, discarding both the highest and lowest measured values. The hydrophobicity of the first layer 405, the second layer 410, or both may be further enhanced with a hydrophobic coating of other materials, such as silicones and fluorocarbons, either as coated from a liquid, or plasma coated.

The first layer 405 and the second layer 410 may also be suitable for bonding to other layers, including each other. For example, the first layer 405, the second layer 410, or both may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene. The first layer 405 and the second layer 410 may include hot melt films.

The area density of the first layer 405 and the second layer 410 may vary according to a prescribed therapy or application. In some embodiments, an area density of less than 40 grams per square meter may be suitable, and an area density of about 20-30 grams per square meter may be particularly advantageous for some applications.

In some embodiments, for example, the first layer 405, the second layer 410, or both may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styrenics, silicones, fluoropolymers, and acetates. A thickness between 20 microns and 100 microns may be suitable for many applications. Films may be clear, colored, or printed. More polar films suitable for laminating to a polyethylene film include polyamide, copolyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations. In some embodiments, the first layer 405 and the second layer 410 may be formed of a transparent polymer to aid in cutting the interface sections 205 apart along the seams 210.

In some embodiments, the first layer 405 and the second layer 410 can be printed with various information, such as product identification, instructions for placement, cutting or sizing, or numbers. For example where each dressing or individual pillow may be numbered. In other embodiments, the manifold sections 215 may be printed.

In some embodiments, the fluid restrictions 220 may comprise or consist essentially of perforations in at least one of the first layer 405 and the second layer 410. Perforations may be formed by removing material from the first layer 405, the second layer 410, or both. For example, perforations may be formed by cutting through the material, which may also deform the edges of the perforations in some embodiments. In the absence of a pressure gradient across the perforations, the passages may be sufficiently small to form a seal or fluid restriction, which can substantially reduce or prevent liquid flow. Additionally or alternatively, one or more of the fluid restrictions 220 may be an elastomeric valve that is normally closed when unstrained to substantially prevent liquid flow, and can open in response to a pressure gradient. A fenestration in the material may be a suitable valve for some applications. Fenestrations may also be formed by removing material, but the amount of material removed and the resulting dimensions of the fenestrations may be an order of magnitude less than perforations, and may not deform the edges. In some embodiments, the fluid restrictions 220 extend through both the first layer 405 and the second layer 410, and the fluid restrictions 220 are coextensive with at least one of the first layer 405 and the second layer 410.

Each of the manifold sections 215 has a length L1, which can be in a range from about 10 mm to about 30 mm (e.g., about 15 mm to about 25 mm or about 18 mm to about 22 mm). For example, each of the manifold sections 215 may have a length of about 20 mm. In some embodiments, the manifold sections 215 may be spaced apart by a distance D1 of about 5 mm to about 15 mm. For example, a distance D1 of about 10 mm may be particularly advantageous for some embodiments. In some embodiments, each of the manifold sections 215 in the tissue interface 114 may be the same size. In other embodiments, one or more of the manifold sections 215 in the tissue interface 114 may have a different size.

In some embodiments, the tissue interface 114 has a thickness T1 ranging from about 5 mm to about 20 mm (e.g., about 8 mm to about 18 mm, or about 10 mm to about 15 mm). For example, the tissue interface 114 may have a thickness T1 of about 8 mm. The thickness T1 of the tissue interface 114 may vary depending upon a thickness of the manifold sections 215 used to form the tissue interface 114. For example, each of the manifold sections 215 may have a thickness ranging from about 5 mm to about 15 mm (e.g., about 8 mm to about 12 mm).

In some embodiments, the tissue interface 114 can be formed by spacing the manifold sections 215 apart, placing the first layer 405 of polymer film over the manifold sections 215, placing the second layer 410 under the manifold sections 215, and bonding the first layer 405 to the second layer 410, forming the seams 210 between the manifold sections 215. Suitable means for bonding the first layer 405 to the second layer 410 may include, for example, an adhesive such as an acrylic, and welding, such as heat, radio frequency (RF), or ultrasonic welding. In some embodiments, sacrificial materials may be disposed between the first layer 405 and the second layer 410 to facilitate welding. Suitable sacrificial materials may include, for example, hot melt films supplied by Bayer (such as H2, HU2, and H5 films), Cornelius (Collano film), or Prochimir (such as TC203 or TC206 film).

In some embodiments, the manifold sections 215 may be formed from an integral manifold material, such as foam. In some embodiments, for example, bonds between the first layer 405 and the second layer 410 may extend through a layer of manifold material to define the manifold sections 215. For example, some embodiments of a manifold layer may have a thickness ranging from about 5 mm to about 8 mm, and at least one of the first layer 405 and the second layer 410 may melt through the manifold layer during welding to form the seams 210.

Additionally or alternatively, a unitary manifold material can be perforated and cut to define the manifold sections 215 in a variety of suitable shapes and patterns. In some embodiments, the seams 210 may align with perforations between the manifold sections 215. In some examples, sacrificial joints may be left between the manifold sections 215 to maintain the manifold sections 215 together as a single unit. Maintaining the manifold sections 215 as a single unit can allow for easier assembly of the tissue interface 114. In some embodiments, either or both of the first layer 405 and the second layer 410 may also be bonded to the manifold sections 215 for additional stability.

Figure 5:
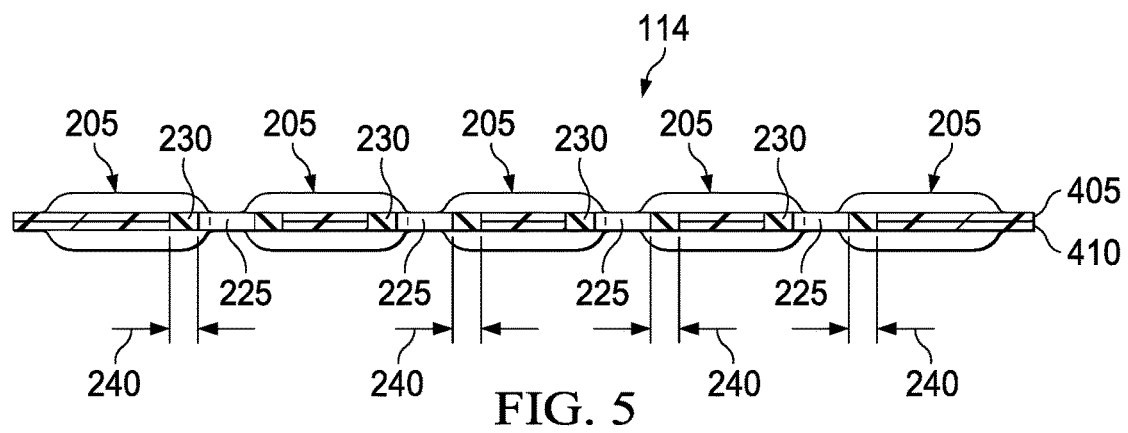
FIG. 5 is a cross-sectional view of the tissue interface of FIG. 3 taken along line 5-5.

FIG. 5 is a sectional view of the tissue interface 114 of FIG. 3 taken along line 5-5, illustrating additional details that may be associated with some embodiments. In some embodiments, the first layer 405 of polymer film can be placed over the manifold sections 215, the second layer 410 can be placed under the manifold sections 215, and the first layer 405 to the second layer 410 can be bonded to each other to form the seams 210 between the manifold sections 215. Suitable means for bonding the first layer 405 to the second layer 410 may include, for example, an adhesive such as an acrylic, and welding, such as heat, radio frequency (RF), or ultrasonic welding. In some embodiments, sacrificial materials may be disposed between the first layer 405 and the second layer 410 to facilitate welding. Suitable sacrificial materials may include, for example, hot melt films supplied by Bayer (such as H2, HU2, and H5 films), Cornelius (Collano film), or Prochimir (such as TC203 or TC206 film). The centers 235 of the openings 225 can be located, and an additional welding process can form the welds 230. In some embodiments, the openings 225 can be cut through the weld 230, removing portions of the first layer 405 and the second layer 410 at the openings 225. In other embodiments, the welds 230 can be formed by bonding the first layer 405 to the second layer 410 in the same process that forms the seams 210.

Figure 6:
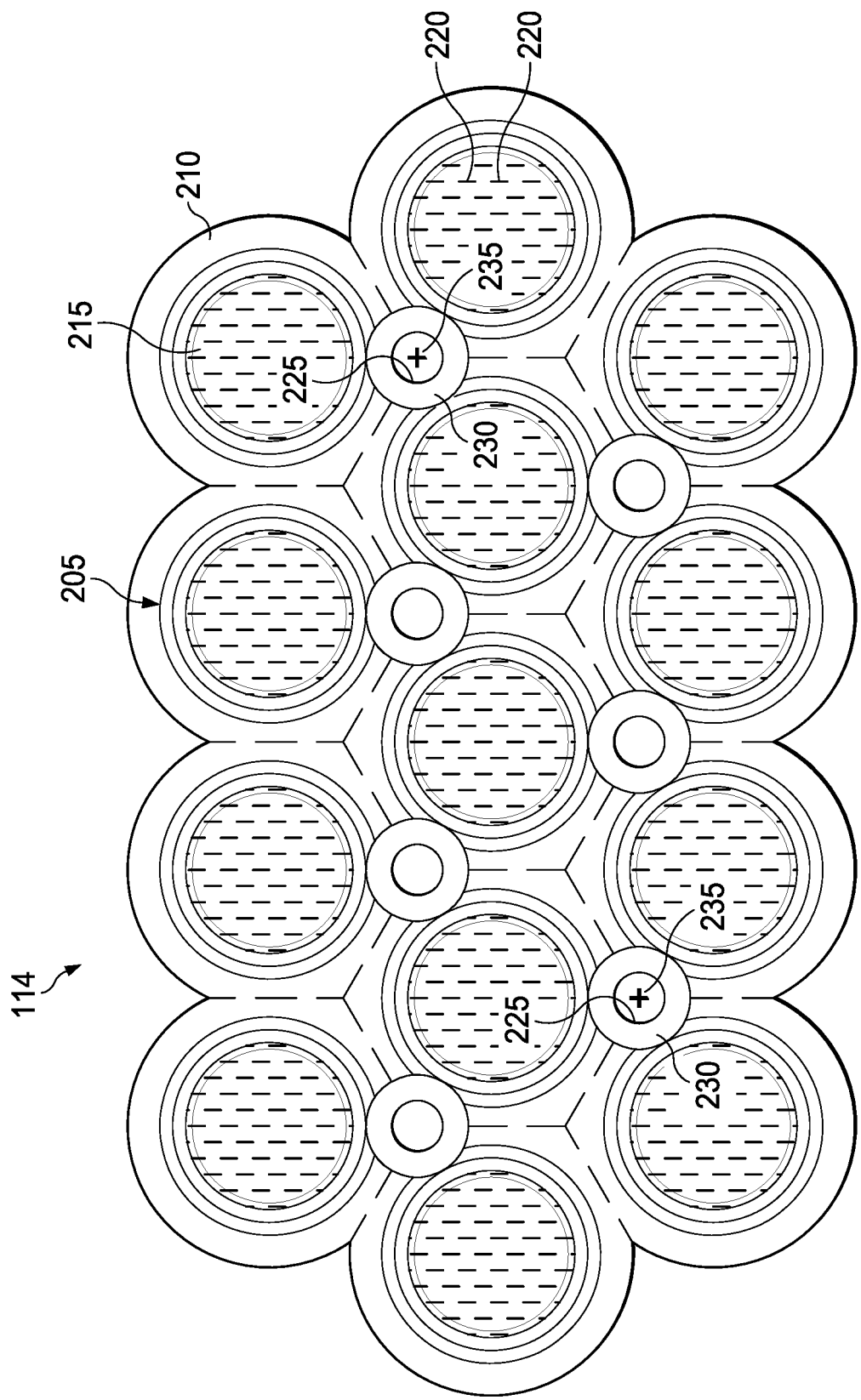
FIG. 6 is a top view of another tissue interface of the dressing of FIG. 2.

FIG. 6 is a top view of another example of the tissue interface 114, illustrating additional details that may be associated with some embodiments. In the example of FIG. 6, the tissue interface 114 has a generally hexagonal shape and each of the interface sections 205 in the tissue interface 114 has a generally circular shape. The tissue interface 114 of FIG. 6 includes thirteen of the interface sections 205 arranged in three rows. The seams 210 can be formed and may generally be tangent to the circular shaped interfaces sections 205. The seams 210 may form hexagons surrounding each interface section 205, so that intersections of seams 210 from adjacent interface sections 205 may have three adjacent interface sections 205. The centers 235 of the openings 225 can be located at the intersections of three adjacent interface sections 205. The tissue interface 114 of FIG. 6 can be formed in a manner similar to the tissue interface 114 of FIGS. 2-5.

Figure 7:
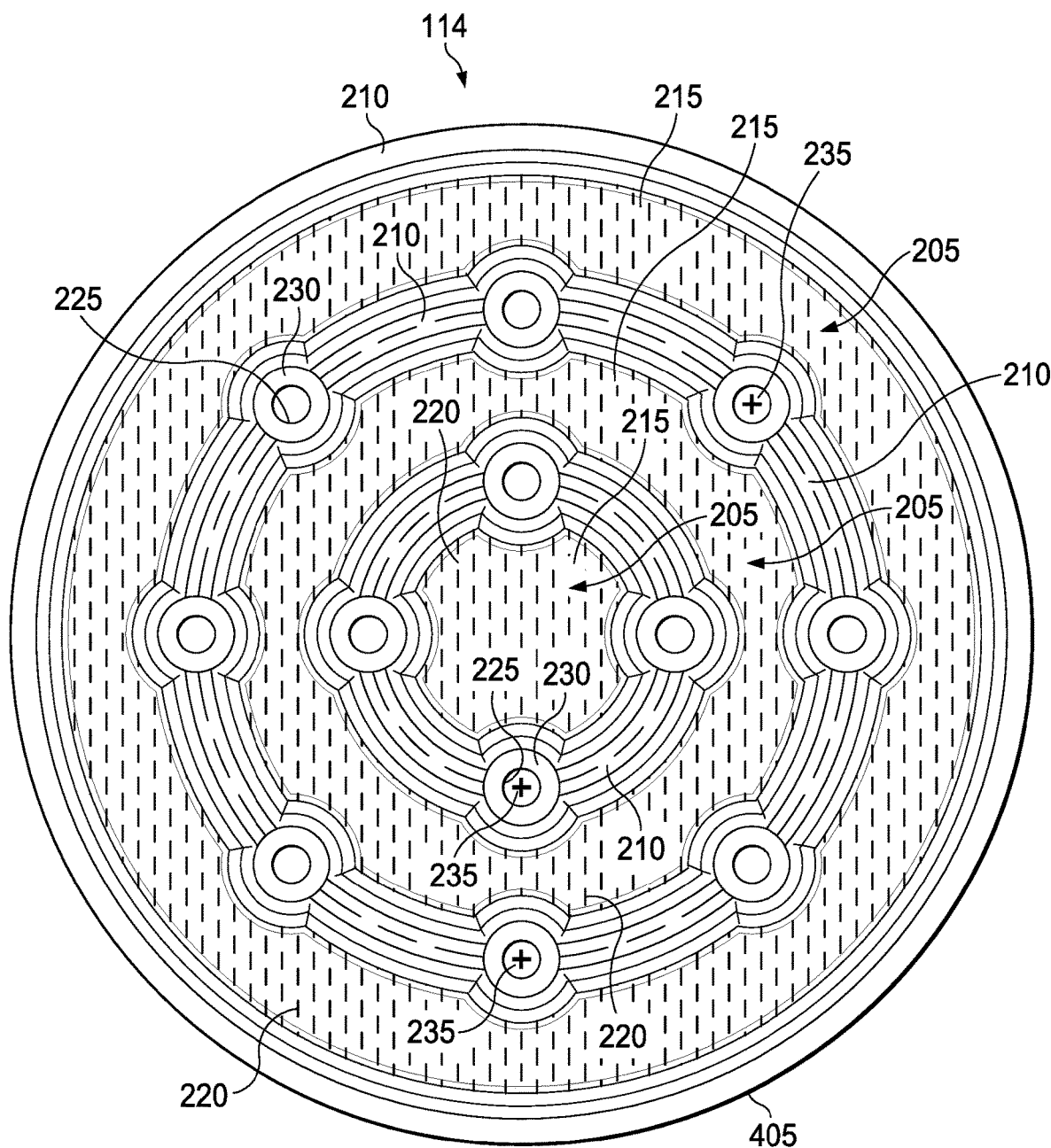
FIG. 7 is a top view of another tissue interface of the dressing of FIG. 2.

FIG. 7 is a top view of another example of the tissue interface 114, illustrating additional details that may be associated with some embodiments. In the example of FIG. 7, the tissue interface 114 has a generally circular shape and the interface sections 205 have generally ring shapes or circular shapes. Each of the manifold sections 215 also has a generally ring shape or circular shape, and can be attached to adjacent manifold sections 215 by the seams 210. The tissue interface 114 of FIG. 7 includes two concentric rings of the interface sections 205 surrounding a circular interface section 205. In some embodiments, the openings 225, bounded by the welds 230, are circumferentially positioned on the seams 210. In some embodiments, the openings 225 can have a circumferential pitch of about 10 mm to about 40 mm. In other embodiments, the openings 225 can be preferentially placed in one portion of the tissue interface 114 so that the openings 225 are unevenly spaced from each other. The tissue interface 114 of FIG. 7 can be formed in a manner similar to the tissue interface 114 of FIGS. 2-5.

Figure 8:
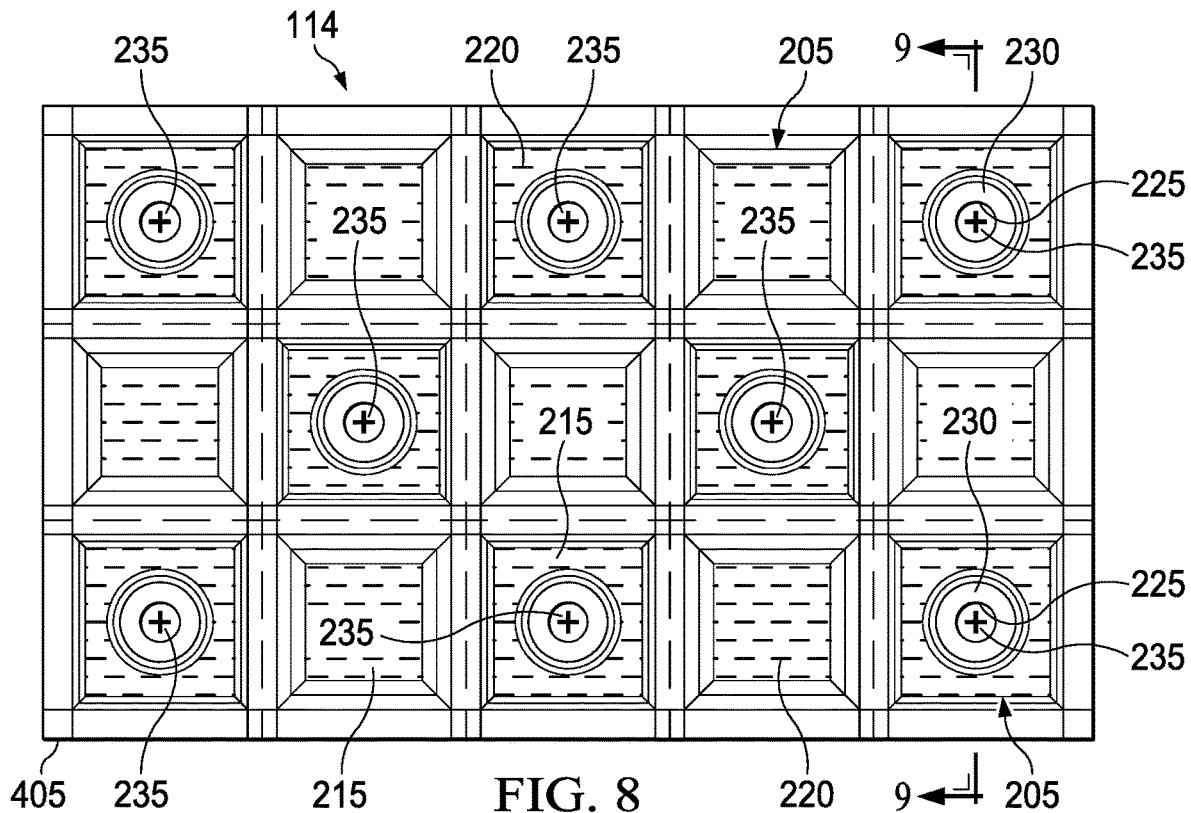
FIG. 8 is a top view of another tissue interface of the dressing of FIG. 2.

FIG. 8 is a top view of another example of the tissue interface 114, illustrating additional details that may be associated with some embodiments. In the example of FIG. 8, the tissue interface 114 can have a rectangular shape and the interface sections 205 can have square shapes. Similar, each of the manifold sections 215 also has a generally square shape, and can be attached to adjacent manifold sections 215 by the seams 210. In some embodiments, the openings 225, bounded by the welds 230, are positioned in the interface sections 205. For example, the centers 235 may be about a center of each manifold section 215. In some embodiments, the openings 225 are dispersed in the tissue interface 114 so that each interface section 205 having an opening 225 is adjacent to an interface section 205 without an opening 225. The arrangement of the openings 225 can manifold fluid across the tissue interface 114 while limiting or preventing a continuous fibrin film from propagating over the tissue interface 114 when multiple layers of the tissue interface 114 are stacked within a deep wound. The discontinuities in the surface of the tissue interface 114 may prevent fibrin film formation if two layers of the tissue interface 114 are aligned. The tissue interface 114 of FIG. 8 can be formed in a manner similar to the tissue interface 114 of FIGS. 2-5.

Figure 9:
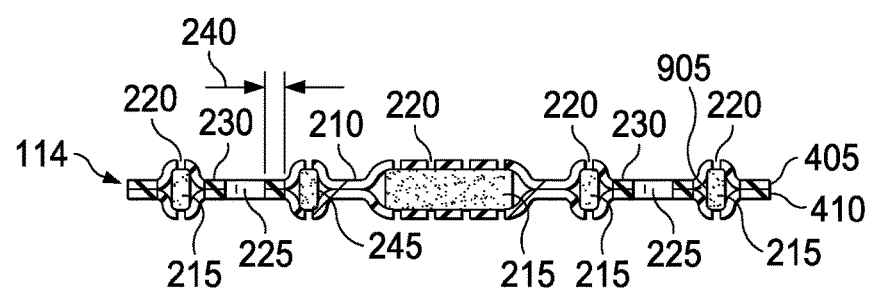
FIG. 9 is a cross-sectional view of the tissue interface of FIG. 8 taken along line 9-9.

FIG. 9 is a sectional view of the tissue interface 114 of FIG. 8 taken along line 9-9, illustrating additional details that may be associated with some embodiments. In the example of FIG. 9, the tissue interface 114 comprises the first layer 405, the second layer 410, and the manifold sections 215 disposed between the first layer 405 and the second layer 410. In some embodiments, the first layer 405 and the second layer 410 may be disposed adjacent to the manifold sections 215 as shown in the example of FIG. 9. Also as shown in the example of FIG. 9, the seams 210 may be formed by one or more bonds between the first layer 405 and the second layer 410. The bonds may be continuous or discrete. The openings 225 can be formed in the interface sections 205. In some embodiments, holes 905 can be formed in the manifold sections 215 prior to the position of the first layer 405 and the second layer 410. The holes 905 can have an average effective diameter between about 1 mm and about 2 mm. The average effective diameter of the openings 225 and the width 240 of the welds 230 can be reduced to fit within the holes 905. The first layer 405 can be bonded to the second layer 410 at the hole 905 in the manifold section 215 to form the welds 230. The openings 225 can be formed in the welds 230. In some embodiments, the manifold section 215 can surround the welds 230 and the openings 225. In some embodiments, bonds between the first layer 405 and the second layer 410 forming the weld 230 may extend through a layer of manifold material of the manifold sections 215. For example, some embodiments of a manifold layer may have a thickness ranging from about 5 mm to about 8 mm, and at least one of the first layer 405 and the second layer 410 may melt through the manifold layer during welding to form the welds 230 and the holes 905.

Figure 10:
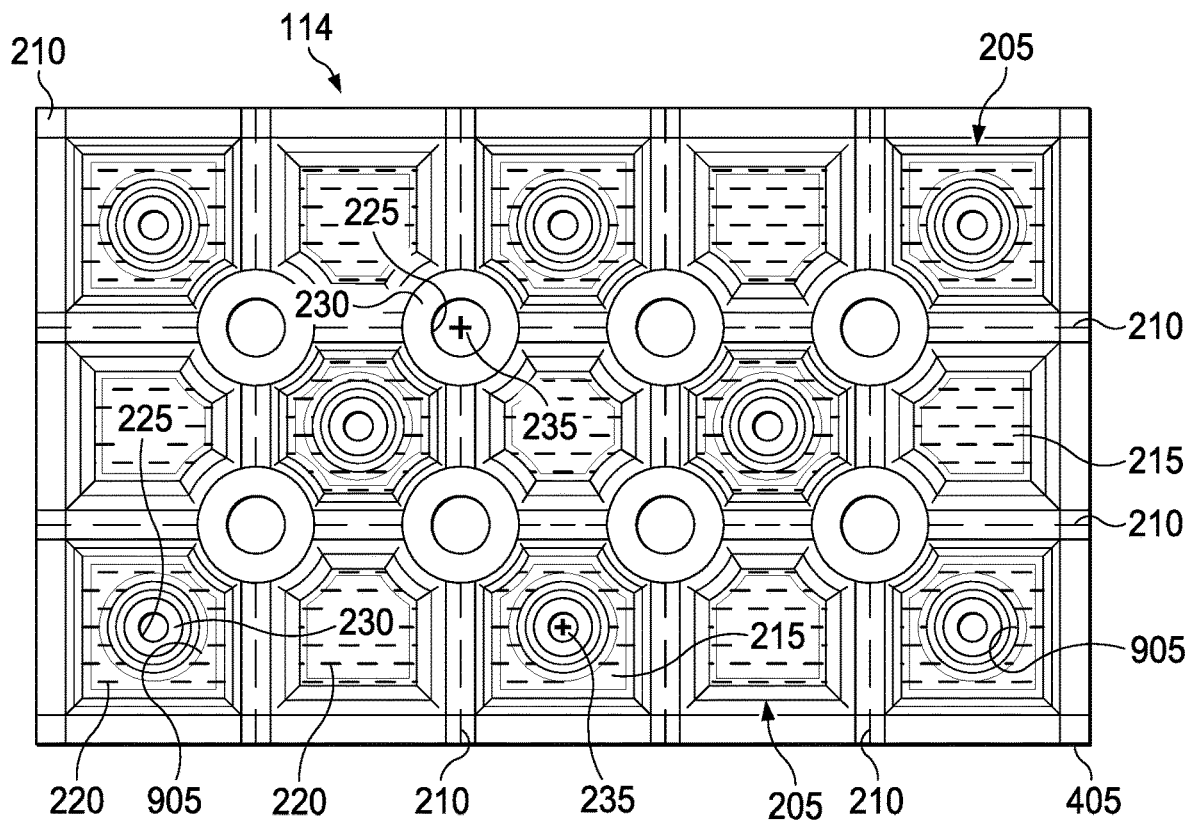
FIG. 10 is a top view of another tissue interface of the dressing of FIG. 2.

FIG. 10 is a top view of another example of the tissue interface 114, illustrating additional details that may be associated with some embodiments. In the example of FIG. 10, the tissue interface 114 has a generally rectangular shape and the interface sections 205 have generally square shapes. Each of the manifold sections 215 also has a generally square shape, and can be attached to adjacent manifold sections 215 by the seams 210. In some embodiments, the openings 225 are disposed in the interface sections 205. For example, the openings 225 are dispersed in the tissue interface 114 so that each interface section 205 having an opening 225 is adjacent to an interface section 205 without an opening 225. In some embodiments, the centers 235 of the openings 225 can also be disposed at the intersections of the seams 210. In some embodiments, the openings 225 disposed in the interface sections 205 can have a different average effective diameter than the openings 225 disposed at the intersections of the seams 210. For example, the openings 225 disposed in the interface sections 205 can have a smaller average effective diameter than the openings 225 disposed at the intersections of the seams 210. In other embodiments, the openings 225 disposed in the interface sections 205 can have a larger average effective diameter than the openings 225 disposed at the intersections of the seams 210. In some embodiments, the openings 225 disposed in the interface sections 205 may be about 5 mm to about 15 mm smaller than the openings 225 disposed at the intersections of the seams 210. The tissue interface 114 of FIG. 10 can be formed in a manner similar to the tissue interface 114 of FIGS. 2-5.

Figure 11:
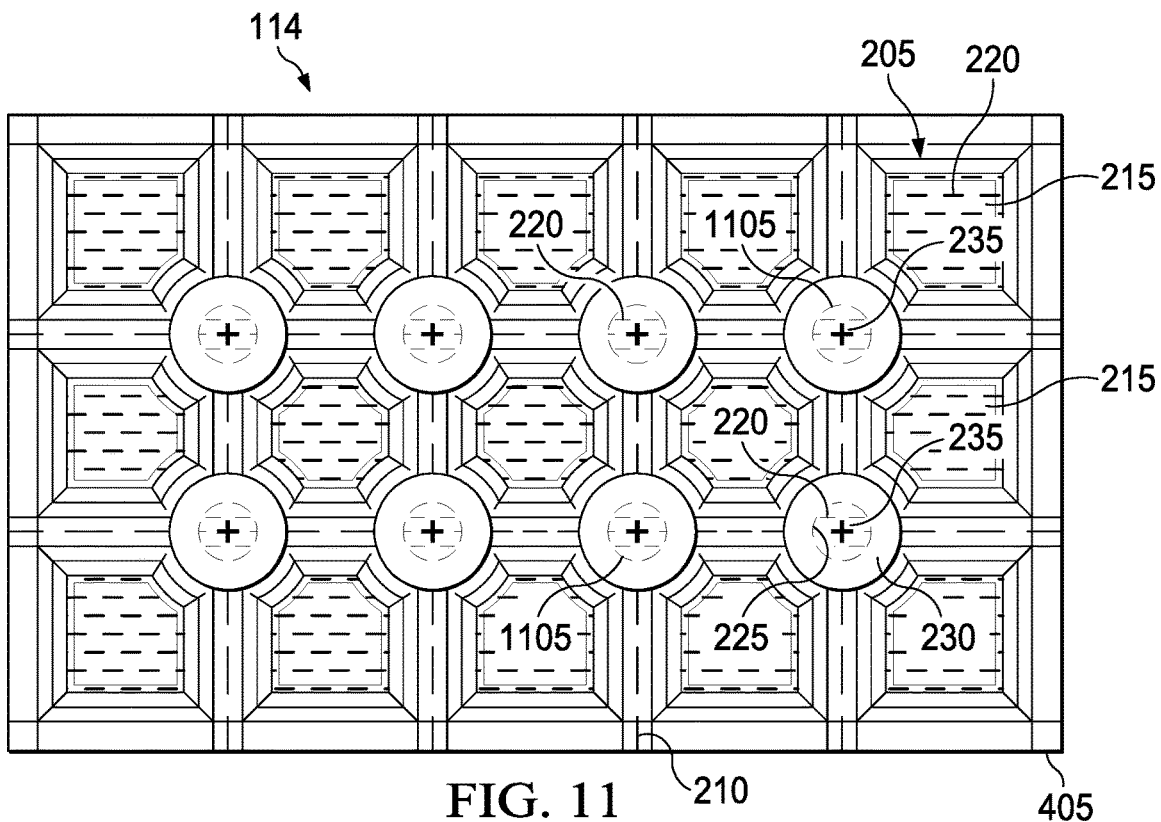
FIG. 11 is a top view of another tissue interface of the dressing of FIG. 2.

FIG. 11 is a top view of another example of the tissue interface 114, illustrating additional details that may be associated with some embodiments. In the example of FIG. 11, the tissue interface 114 has a generally rectangular shape and the interface sections 205 have generally square shapes. Each of the manifold sections 215 also has a generally square shape, and can be attached to adjacent manifold sections 215 by the seams 210. In some embodiments, the centers 235 are at the intersections of the seams 210 that are orthogonal to each other. The welds 230 can be formed by welding, bonding, adhering or otherwise coupling the first layer 405 to the second layer 410. In some embodiments, the first layer 405 and the second layer 410 remain intact following formation of the welds 230. Each weld 230 can include a tear line 1105. The tear line 1105 can be a circle of perforations in the weld 230 having an average effective diameter that is about the average effective diameter of the opening 225. In some embodiments, the tear line 1105 may be a line of separation. For example, the tear line 1105 can allow the removal of the first layer 405 and the second layer 410 of the weld 230 inboard of the tear line 1105, forming an opening 225. In this manner, the clinician can determine the appropriate areas to permit fluid flow across the tissue interface 114. For example, a clinician may determine that a portion of the tissue site may have necrotic tissue or slough and another portion of the tissue site may be free from necrotic tissue or slough. The clinician may create the openings 225 along the tear lines 1105 over the areas of necrotic tissue or slough, leaving the welds 230 in the remaining areas of the tissue interface 114 intact along the tear lines 1105. In some embodiments, the first layer 405 and the second layer 410 at each center 235 may include the fluid restrictions 220 inboard of the tear line 1105. In other embodiments, the first layer 405 and the second layer 410 may be free of the fluid restrictions 220 inboard of the tear line 1105. The tissue interface 114 of FIG. 11 can be formed in a manner similar to the tissue interface 114 of FIGS. 2-5.

Figure 12:
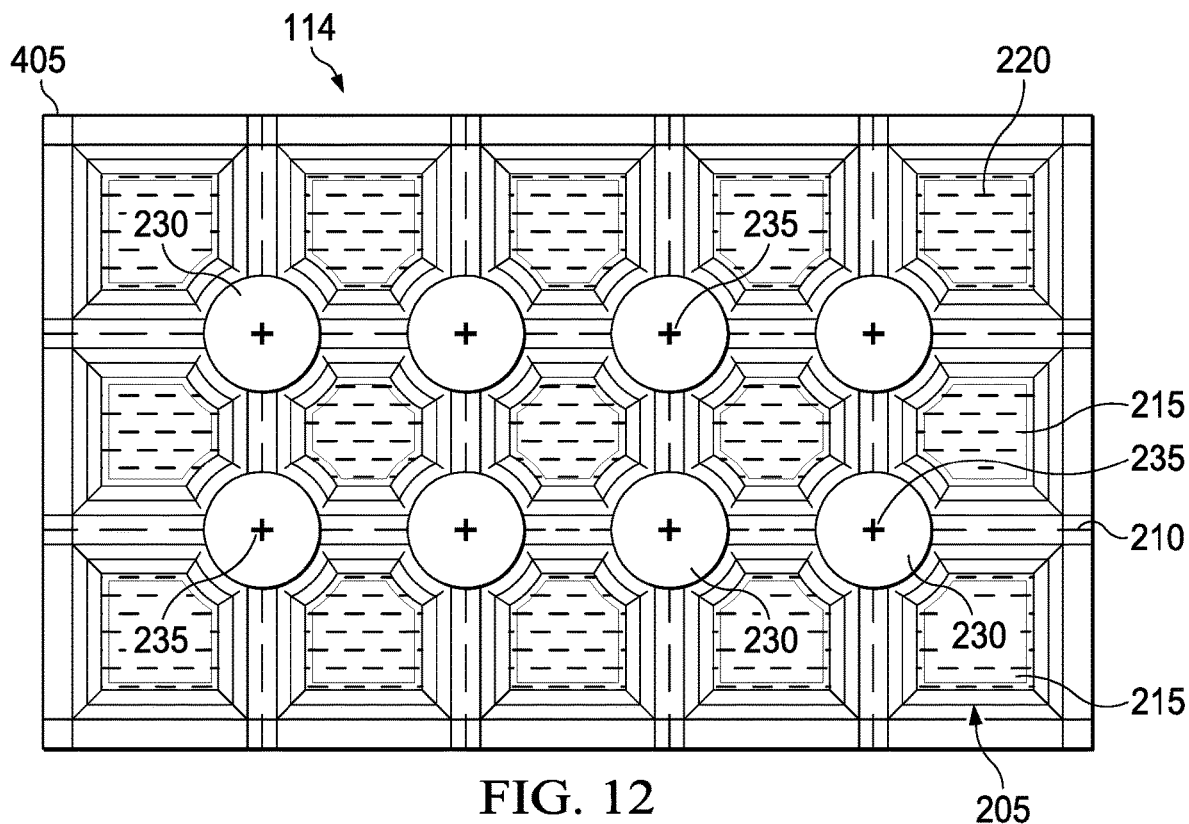
FIG. 12 is a top view of another tissue interface of the dressing of FIG. 2.

FIG. 12 is a top view of another example of the tissue interface 114, illustrating additional details that may be associated with some embodiments. In the example of FIG. 12, the tissue interface 114 has a generally rectangular shape and the interface sections 205 have generally square shapes. Each of the manifold sections 215 also has a generally square shape, and can be attached to adjacent manifold sections 215 by the seams 210. In some embodiments, the centers 235 are at the intersections of the seams 210 that are orthogonal to each other. The welds 230 can be formed by welding, bonding, adhering or otherwise coupling the first layer 405 to the second layer 410. In some embodiments, the first layer 405 and the second layer 410 remain intact following formation of the welds 230. For example, the first layer 405 and the second layer 410 can be left coupled to each other to form the weld 230 and intact following the coupling process. The first layer 405 and the second layer 410 can be free of the fluid restrictions 220 at the welds 230. In some embodiments, the first layer 405 and the second layer 410 can be cut at the weld 230 by a clinician. For example, a clinician may use scissors or another cutting device to form the openings 225 in the welds 230 prior to application of the tissue interface 114 to a tissue site. In this manner, the clinician can determine the appropriate areas to permit fluid flow across the tissue interface 114. The tissue interface 114 of FIG. 12 can be formed in a manner similar to the tissue interface 114 of FIGS. 2-5.

Figure 13:
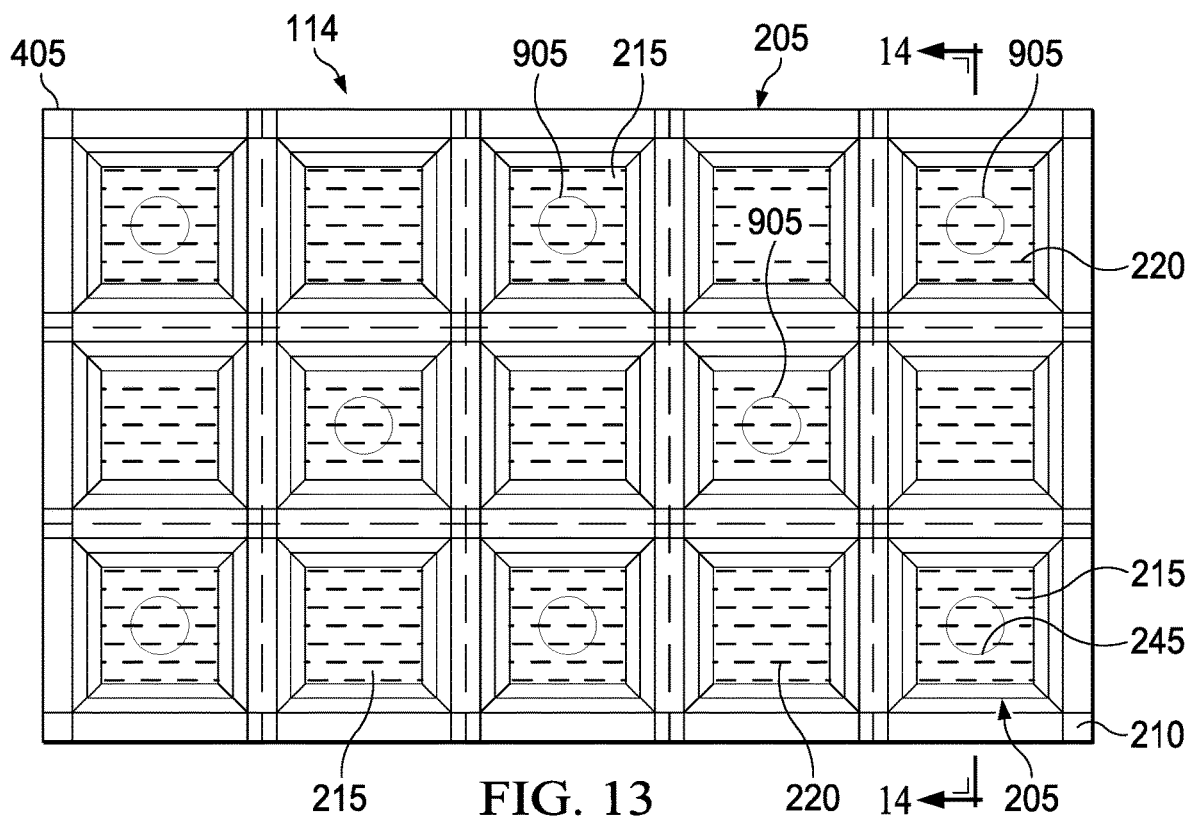
FIG. 13 is a top view of another tissue interface of the dressing of FIG. 2.

FIG. 13 is a top view of another example of the tissue interface 114, illustrating additional details that may be associated with some embodiments. In some embodiments, the holes 905 can be formed in the manifold sections 215, and the manifold sections 215 can be enclosed in the first layer 405 and the second layer 410. For example, the hole 905 can be formed at about a center of the manifold section 215. The seams 210 can be formed to separate the manifold sections 215 into the interface sections 205. The restrictions 220 can be formed in the first layer 405 and the second layer 410. In some embodiments, additional restrictions 220 can be positioned over the holes 905, increasing fluid flow through the holes 905 while reducing the localized raised granulation that can occur under the holes 905. The tissue interface 114 of FIG. 13 can be formed in a manner similar to the tissue interface 114 of FIGS. 2-5.

Figure 14:
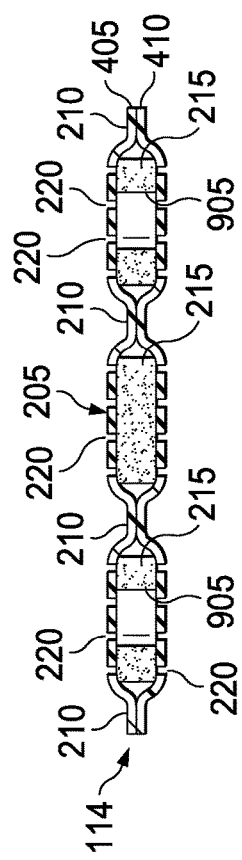
FIG. 14 is a cross-sectional view of the tissue interface of FIG. 13 taken along line 14-14.

FIG. 14 is a sectional view of the tissue interface 114 of FIG. 13 taken along line 14-14, illustrating additional details that may be associated with some embodiments. In the example of FIG. 14, the tissue interface 114 comprises the first layer 405, the second layer 410, and the manifold sections 215 disposed between the first layer 405 and the second layer 410. In some embodiments, the first layer 405 and the second layer 410 may be disposed adjacent to the manifold sections 215 as shown in the example of FIG. 14. Also as shown in the example of FIG. 14, the seams 210 may be formed by one or more bonds between the first layer 405 and the second layer 410. The bonds may be continuous or discrete. In some embodiments, the holes 905 can be formed in the manifold sections 215 prior to positioning of the first layer 405 and the second layer 410. The first layer 405 and the second layer 410 can be free from bonds at the holes 905. In some embodiments, the fluid restrictions 220 can be formed in the first layer 405 and the second layer 410 over the holes 905 of the manifold sections 215.

Figure 15:
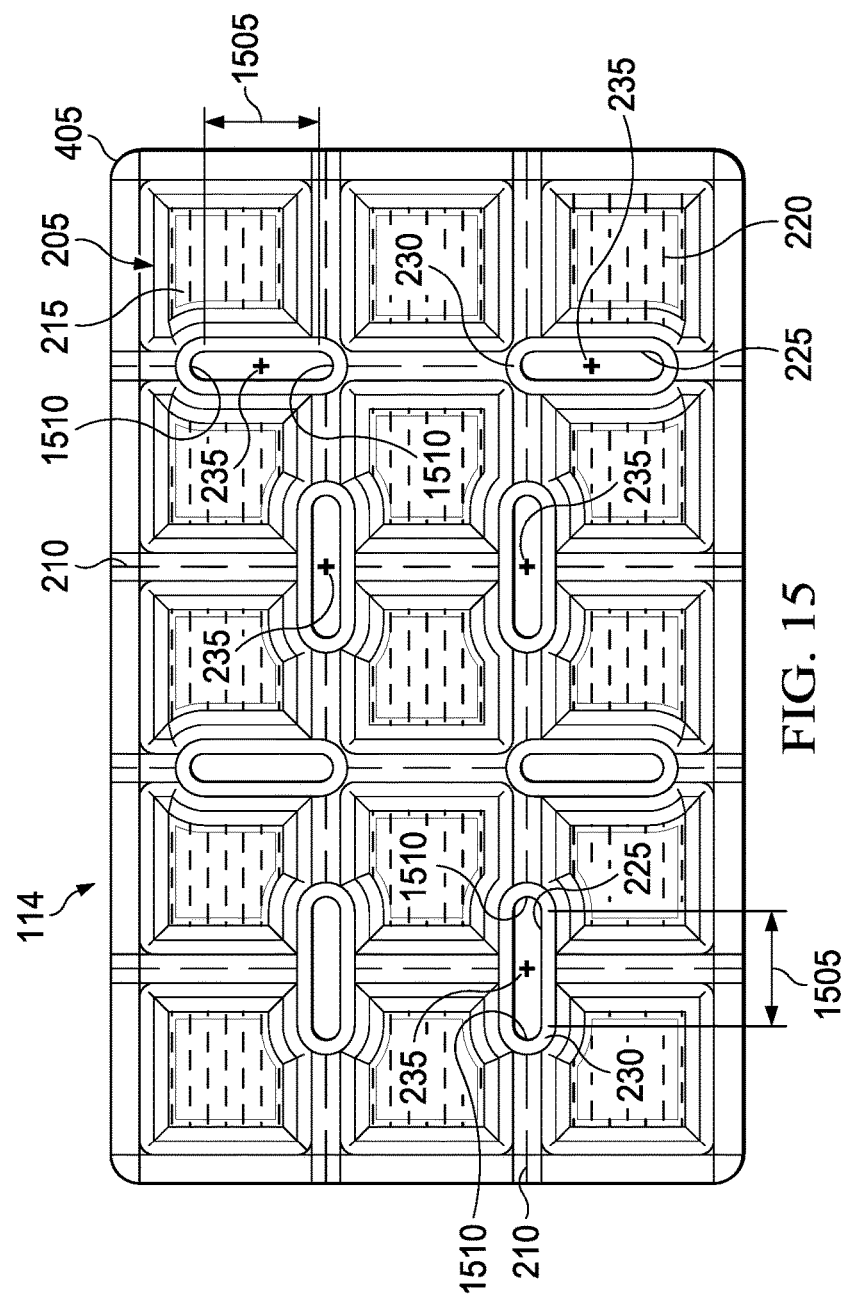
FIG. 15 is a top view of another tissue interface of the dressing of FIG. 2.

FIG. 15 is a top view of another example of the tissue interface 114, illustrating additional details that may be associated with some embodiments. In some embodiments, the openings 225 and the welds 230 can be elongated, having an ovular shape. For example, each opening 225 may have a length 1505 and two portions 1510 that are semi-circular. A portion 1510 can be located at each end of the length 1505. The portions 1510 of the openings 225 and can have an average effective diameter between about 5 mm and about 10 mm, and the length 1505 can be between about 10 mm and about 30 mm. In some embodiments, the centers 235 of the openings 225 can be at intersections of the seams 210 that are orthogonal. For example, the openings 225 can be positioned on the seams 210 parallel to the length of the tissue interface 114 at the intersection of the seams 210 parallel to the width of the tissue interface 114. In other embodiments, the centers 235 can be offset from the intersections of the seams 210 that are orthogonal. For example, the centers 235 can be positioned on the seams 210 that are parallel to the width of the tissue interface 114 and offset from the seams 210 that are parallel to the length of the tissue interface 114. The tissue interface 114 of FIG. 15 can be formed in a manner similar to the tissue interface 114 of FIGS. 2-5.

Figure 16:
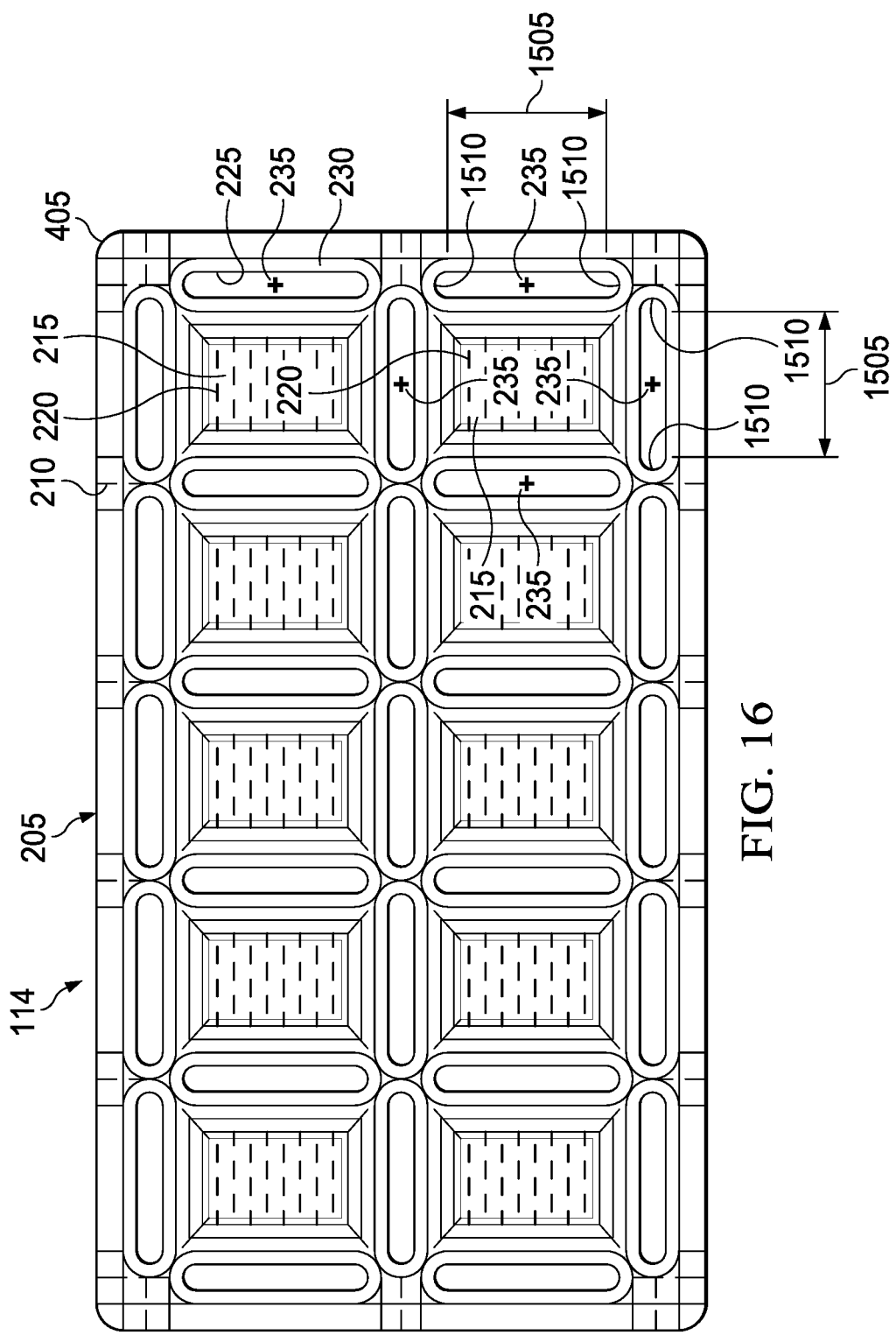
FIG. 16 is a top view of another tissue interface of the dressing of FIG. 2.

FIG. 16 is a top view of another example of the tissue interface 114, illustrating additional details that may be associated with some embodiments. In some embodiments, the openings 225 and the welds 230 can be elongated. For example, each opening 225 may have the length 1505 and two portions 1510 that are semi-circular. A portion 1510 can be located at each end of the length 1505. The portions 1510 of the openings 225 and can have an average effective diameter between about 5 mm and about 10 mm, and the length 1505 can be between about 20 mm to about 40 mm. In some embodiments, the centers 235 of each opening 225 can be about a center of an adjacent manifold section 215. The length 1505 of the openings 225 can be such that ends of the welds 230 may be adjacent to each other. In some embodiments, the ends of the welds 230 that are elongated may contact each other to form a mesh. For example, the openings 225 can have an average effective diameter of about 50 mm. Fluid may freely flow across the tissue interface 114 through the openings 225. In some embodiments, the manifold sections 215 can be separated from each other prior to encapsulation in the first layer 405 and the second layer 410, providing a more even structure and reducing uneven granulation formation. In other embodiments, the manifold sections 215 can be separated from each other during encapsulation by the first layer 405 and the second layer 410. The tissue interface 114 of FIG. 16 can be formed in a manner similar to the tissue interface 114 of FIGS. 2-5.

In other embodiments, the tissue interface 114 may include more or fewer of the interface sections 205. Each of the interface sections 205 may have a different size or a same size. Each of the interface sections 205 may have a same shape or a different shape. For example, the interface sections 205 may be in the form of equilateral polygons, which may have sides not exceeding about 20 millimeters and having an area less than about 400 square millimeters.

In some embodiments, a method for treating a tissue site may include excising separable sections of a dressing based upon at least one of a size and shape of the tissue site being treated. The method may also include applying the dressing to fill and/or cover the tissue site, and sealing the dressing to epidermis adjacent to the tissue site. The method may further include fluidly coupling the dressing to a negative-pressure source, and applying negative pressure from the negative-pressure source to the dressing.

In some embodiments, excising separable sections may comprise cutting a seam or a seal between the separable sections. In some configurations, the separable sections may be excised without exposing a manifold section inside the dressing.

In some embodiments, applying negative pressure from the negative-pressure source to the dressing can include drawing tissue into the openings of the tissue interface. The method may rupture or otherwise disrupt the tissue drawn into the openings, aiding in the removal of necrotic tissue or slough.

The systems, apparatuses, and methods described herein may provide significant advantages. For example, in some embodiments, the seams 210 may be wide enough to allow the interface sections 205 to be cut apart or otherwise separated so as to obtain a tissue interface 114 having a desired size and shape. For example, tissue interface 114 can be sized and shaped to fill deep and/or irregular wounds by separating the interface sections 205. Moreover, some embodiments of the dressing 104 may be worn for about 3 to about 10 days (e.g., about 7 days). The tissue interface 114 can provide improved flexibility and fewer uneven granulation effects. The tissue interface 114 can be used as both the wound and periwound interface. The tissue interface 114, while sizeable, can also be subjected to less sizing and placed over an intact periwound with little to no negative impact on the periwound. In some embodiments, the tissue interface 114 can permit the user to customize the openings 225, choosing to release the openings 225 in desired areas while leaving the openings 225 closed in undesired areas.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 108 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, the dressing comprising:
    a manifold having a first surface and a second surface opposite the first surface;
    a first layer adjacent to the first surface and a second layer adjacent to the second surface, the first layer and the second layer each comprising a polymer film;
    a plurality of fluid restrictions in the polymer film adjacent to at least the first surface;
    a first plurality of bonds between the first layer and the second layer, the first plurality of bonds defining separable sections of the manifold, the first plurality of bonds comprising intersecting linear bonds; and
    a second plurality of bonds between the first layer and the second layer, the second plurality of bonds defining a plurality of openings and being located at intersections of the first plurality of bonds.

2. The dressing of claim 1, wherein the first plurality of bonds form seams between the separable sections of the manifold.

3. The dressing of claim 1, wherein the first plurality of bonds form seams having a width of at least 2 millimeters between the separable sections of the manifold.

4. The dressing of claim 1, wherein the first plurality of bonds form seams having a width of at least 2 millimeters and less than 5 millimeters between the separable sections of the manifold.

5. The dressing of claim 1, wherein:
    the openings are circular.

6. The dressing of claim 1, wherein:
    the second plurality of bonds comprises a first portion and a second portion;
    the first portion of the second plurality of bonds are located at the intersections of the first plurality of bonds; and
    the second portion of the second plurality of bonds are displaced from the first plurality of bonds.

7. The dressing of claim 1, wherein:
    a first portion of the plurality of openings has a first average effective diameter; and
    a second portion of the plurality of openings has a second average effective diameter, the second average effective diameter being different than the first average effective diameter.

8. The dressing of claim 1, wherein the manifold comprises perforations aligned with the first plurality of bonds.

9. The dressing of claim 1, wherein the manifold comprises perforations between the separable sections.

10. The dressing of claim 1, wherein the manifold comprises:
    perforations aligned with the first plurality of bonds; and
    sacrificial joints between the separable sections.

11. The dressing of claim 1, wherein the first plurality of bonds form a seal between the separable sections of the manifold.

12. The dressing of claim 1, wherein the first plurality of bonds form a seal between the separable sections of the manifold, the seal configured to be cut without exposing the manifold.

13. The dressing of claim 1, wherein the plurality of openings extend through the manifold, the first layer, and the second layer.

14. The dressing of claim 1, wherein each opening of the plurality of openings is elongated.

15. The dressing of claim 14, wherein the ends of the second plurality of bonds are elongated and contact each other to form a mesh.

16. The dressing of claim 1, wherein the plurality of second bonds are perforated.

* * * * *